US 11,278,195 B2

(12) United States Patent
Oka

(10) Patent No.: US 11,278,195 B2
(45) Date of Patent: Mar. 22, 2022

(54) ILLUMINATION OPTICAL SYSTEM

(71) Applicant: OLYMPUS CORPORATION, Hachioji (JP)

(72) Inventor: Tetsuhiro Oka, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/457,124

(22) Filed: Jun. 28, 2019

(65) Prior Publication Data

US 2019/0313891 A1 Oct. 17, 2019

Related U.S. Application Data

(63) Continuation of application No. PCT/JP2017/000162, filed on Jan. 5, 2017.

(51) Int. Cl.
*A61B 1/07* (2006.01)
*F21V 8/00* (2006.01)
*A61B 1/00* (2006.01)
*G02B 5/02* (2006.01)

(52) U.S. Cl.
CPC ............ *A61B 1/07* (2013.01); *A61B 1/00096* (2013.01); *G02B 5/0242* (2013.01); *G02B 6/0008* (2013.01)

(58) Field of Classification Search
CPC .... G02B 6/0008; G02B 6/004; G02B 6/0041; G02B 5/0242; A61B 1/07; A61B 1/00096
See application file for complete search history.

(56) References Cited

U.S. PATENT DOCUMENTS

| 6,999,234 B2* | 2/2006 | Hiraishi | G02B 5/0268 |
| | | | 359/489.12 |
| 2005/0018431 A1 | 1/2005 | Shiang | |
| 2007/0206391 A1 | 9/2007 | Matsuo et al. | |
| 2012/0051693 A1* | 3/2012 | Yoshida | G02B 5/02 |
| | | | 385/31 |
| 2016/0100750 A1* | 4/2016 | Furuta | G02B 23/2423 |
| | | | 362/558 |

FOREIGN PATENT DOCUMENTS

| CN | 1823433 A | 8/2006 | |
| CN | 100520458 C | 7/2009 | |
| EP | 1830123 A1 | 9/2007 | |
| JP | 2013058454 A | 3/2013 | |
| JP | 2013161645 A | 8/2013 | |
| JP | 2014094123 A | 5/2014 | |
| JP | 2015016020 A | 1/2015 | |
| JP | 201516020 A * | 1/2019 | ............... G02B 5/02 |
| WO | 2005018010 A2 | 2/2005 | |
| WO | 2015005108 A1 | 1/2015 | |

OTHER PUBLICATIONS

International Search Report (ISR) dated Mar. 28, 2017 issued in International Application No. PCT/JP2017/000162.
Written Opinion dated Mar. 28, 2017 issued in International Application No. PCT/JP2017/000162.

* cited by examiner

*Primary Examiner* — Arman B Fallahkhair
(74) *Attorney, Agent, or Firm* — Holtz, Holtz & Volek PC

(57) ABSTRACT

An illumination optical system includes a diffusion element that diffuses illumination light entering from a light source, the diffusion element emitting the illumination light. The diffusion element is formed by dispersing fine particles of at least one kind in a homogeneous medium that is made of a material different from the fine particles, and the diffusion element satisfies a specific conditional expressions.

13 Claims, 16 Drawing Sheets

ILLUMINATION OPTICAL SYSTEM

CROSS-REFERENCE TO RELATED APPLICATIONS

This is a continuation of International Application PCT/JP2017/000162, with an international filing date of Jan. 5, 2017, which is hereby incorporated by reference herein in its entirety.

TECHNICAL FIELD

The present invention relates to an illumination optical system.

BACKGROUND ART

There is a known endoscope that has a wide angle of view of 180° or more, thus allowing simultaneous observation in forward, side, and rear fields of view (for example, see PTL 1).

An illumination optical system in the endoscope of PTL 1 includes a cylinder-shaped diffusion layer and a reflecting surface provided on an inner surface of the diffusion layer, and diffuses, inside the diffusion layer, illumination light that is made to enter from one end of the diffusion layer in the axial direction thereof, thereby making it possible to uniformly illuminate a wide region.

CITATION LIST

Patent Literature

{PTL 1} Japanese Unexamined Patent Application, Publication No. 2015-16020

SUMMARY OF INVENTION

One aspect of the present invention provides an illumination optical system including a diffusion element that diffuses illumination light entering from a light source, the diffusion element emitting the illumination light, wherein the diffusion element is formed by dispersing fine particles of at least one kind in a homogeneous medium that is made of a material different from the fine particles, and the diffusion element satisfies the following conditional expressions:

$0.06 \leq \mu s(1/mm) \leq 20$; and $0.5 \leq g < 1$, where $\mu s$ is a scattering coefficient of the diffusion element, and $g$ is an anisotropy parameter of the fine particles in the homogeneous medium.

DESCRIPTION OF EMBODIMENTS

An illumination optical system 30 according to one embodiment of the present invention will be described below with reference to the drawings.

The illumination optical system 30 of this embodiment is provided at a distal end of an insertion portion 2 of an endoscope 1.

Figure 1:
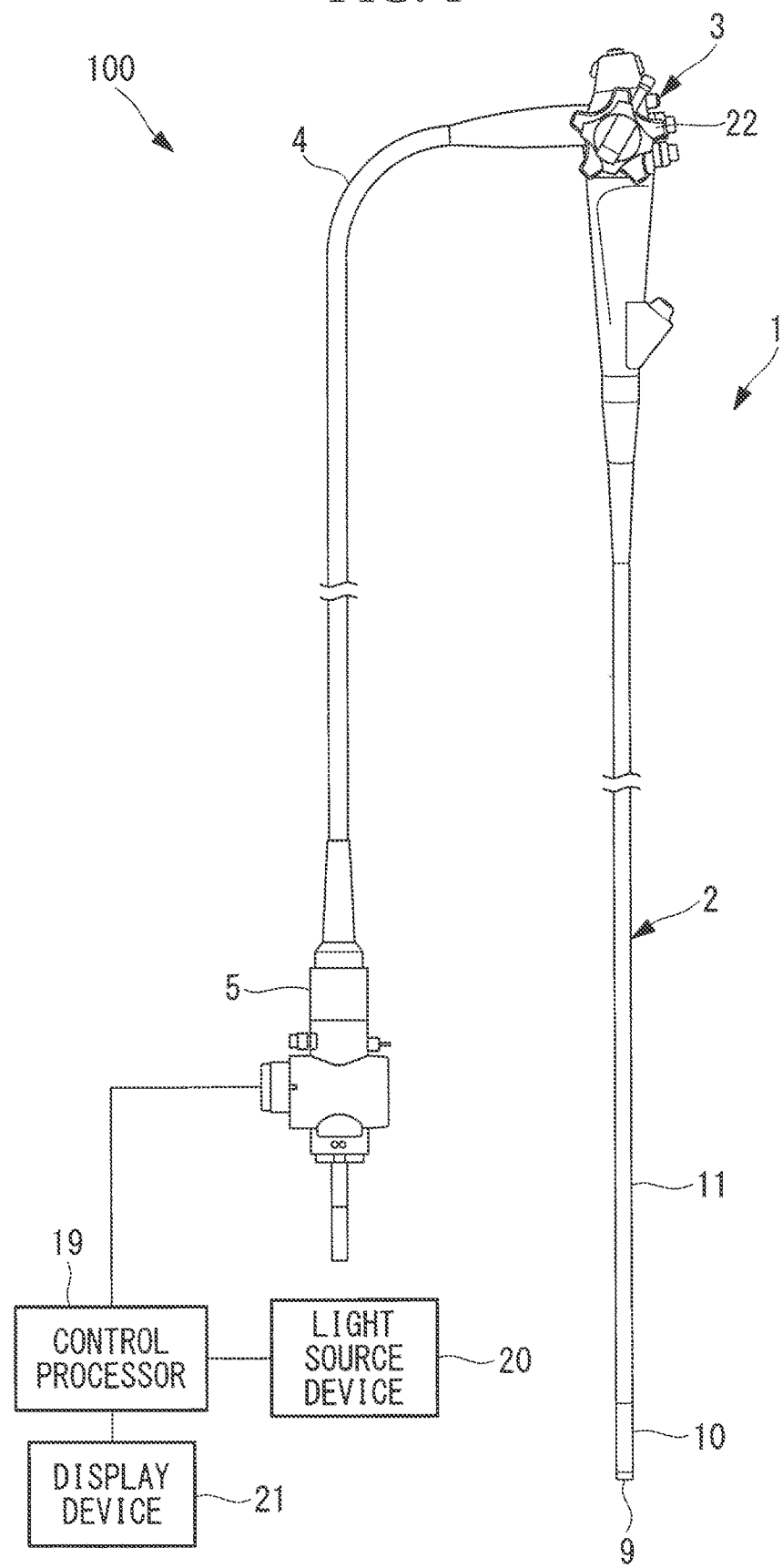
FIG. 1 is a view showing the overall configuration of an endoscope that is provided with an illumination optical system according to one embodiment of the present invention.

As shown in FIG. 1, the endoscope 1 is provided with: the elongated insertion portion 2, which is inserted into a body cavity or the like; an operation part 3 that is provided at a base end of the insertion portion 2; a universal cord 4 that extends from the operation part 3; and a connector part 5 that is provided at an end of the universal cord 4.

Figure 2:
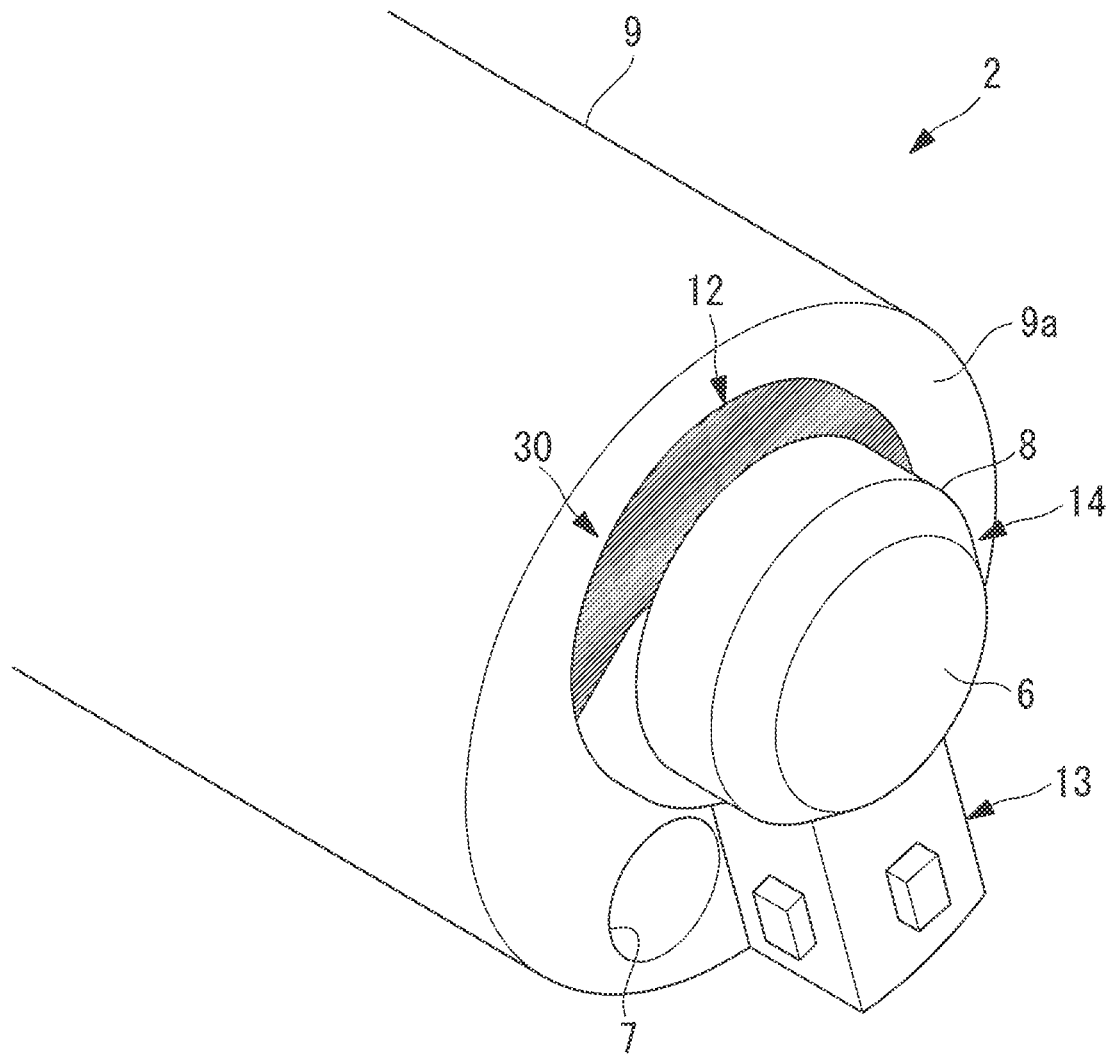
FIG. 2 is a perspective view showing, in an enlarged manner, a part of a distal-end section of the endoscope shown in FIG. 1.
Figure 3:
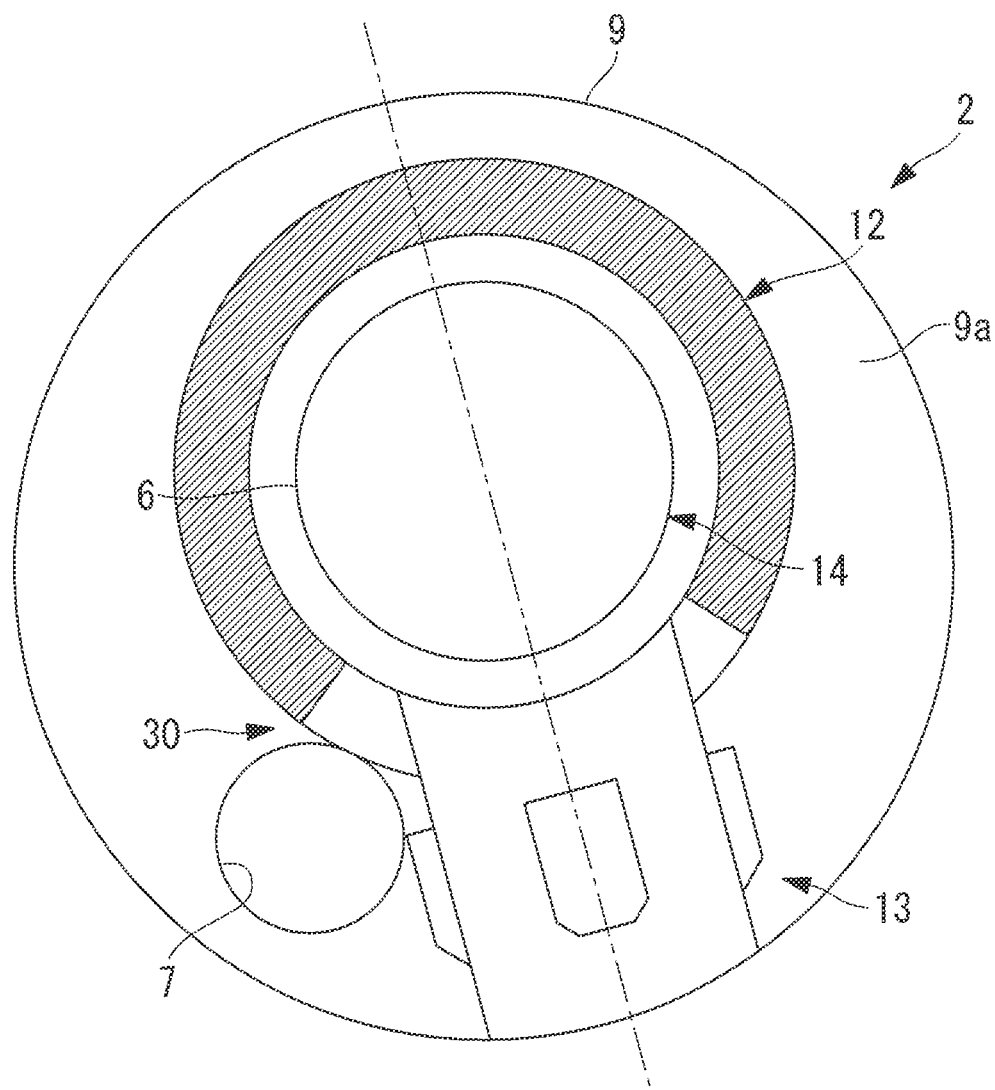
FIG. 3 is a front view showing the distal-end section of the endoscope shown in FIG. 2.
Figure 4:
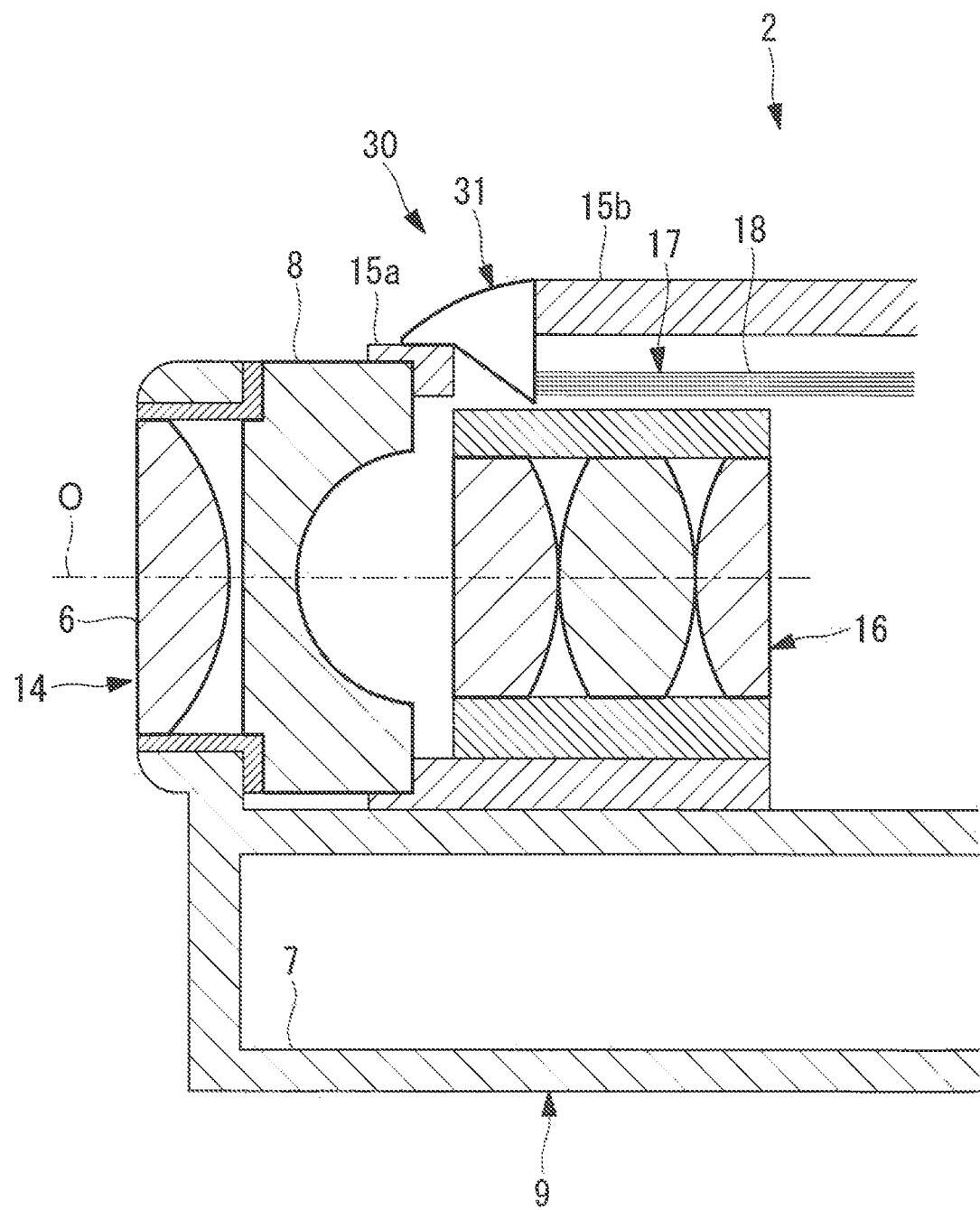
FIG. 4 is a partial longitudinal sectional view showing the distal-end section of the endoscope shown in FIG. 2.

As shown in FIGS. 2 to 4, at the distal end of the insertion portion 2, a forward-observation objective lens 6 for direct viewing is disposed on a distal-end surface 9a so as to be directed toward a front side, and a side-observation objective lens 8 for side-viewing and an illumination lens 12 are disposed in the vicinity of the forward-observation objective lens 6. Accordingly, the endoscope 1 has such a wide angle of view as to be able to observe a forward field of view and a side field of view at the same time.

The forward-observation objective lens 6 forms an image of an observation target located in front of the insertion portion 2. Furthermore, the side-observation objective lens 8 is formed into a substantially cylindrical shape so as to form an image of an observation target located at a lateral side of the insertion portion 2. The side-observation objective lens 8 is disposed closer to the base end of the insertion portion 2 than the forward-observation objective lens 6 is.

The insertion portion 2 is provided with: a rigid distal-end section 9 that is provided at the most distal end section; a bending section 10 that is connected to the base end of the distal-end section 9; and a flexible tube section 11 that is connected to the base end of the bending section 10 and that is formed of a long tubular member having flexibility.

As shown in FIGS. 2 and 3, a treatment-tool channel opening 7, the forward-observation objective lens 6, the illumination lens 12, a water-supply nozzle 13, etc., are disposed on the distal-end surface 9a of the distal-end section 9.

As shown in FIG. 4, an image-capturing optical system 14 and the illumination optical system 30 are disposed in the distal-end section 9 of the insertion portion 2. The image-capturing optical system 14 is provided with: the forward-observation objective lens 6, which is disposed at the front of a section protruding from the distal-end surface 9a; the side-observation objective lens 8, which is exposed on the side surface around the protruding section; an image-formation optical system 16 that is accommodated in the distal-end section 9; and an imaging device (not shown) that captures an image of an observation target formed by the image-formation optical system 16. Note that details other than the image-capturing optical system 14 and the illumination optical system 30 are not shown in FIG. 4.

A treatment-tool channel, a light guide 17, a signal cable (not shown), etc. are disposed in the insertion portion 2. The treatment-tool channel extends from the treatment-tool channel opening 7 on the distal-end surface 9a to a treatment-tool insertion port that is disposed in the vicinity of a connection part located between the insertion portion 2 and the operation part 3, while penetrating through the insertion portion 2 in the longitudinal direction. Furthermore, the light guide 17 and the signal cable penetrate through the insertion portion 2 in the longitudinal direction from the distal-end section 9 of the insertion portion 2, pass through the inside of the universal cord 4 via the inside of the operation part 3, and are eventually connected to the connector part 5, which is located at the end of the universal cord 4.

The light guide 17 is formed of a fiber bundle 18 formed by bundling a plurality of light guide fibers for guiding illumination light.

The universal cord 4 is connected to a control processor 19, a light source device (light source) 20, and a display device 21, which are external devices, via the connector part 5, thereby constituting an endoscope system 100.

The operation part 3 is a part to be gripped by a user when the user uses the endoscope 1, and a bending-operation nob 22 and a plurality of operation members for handling the other various operations are disposed on an exterior surface of the operation part 3. Here, for example, the bending-operation nob 22 is an operation member for bending the bending section 10 of the insertion portion 2 in a desired upper, lower, left, or right direction, by being rotationally operated by the user with his/her fingers.

The light source device 20 is a device for generating illumination light. The control processor 19 is a signal processing device that integrally controls the entirety of the endoscope system 100. The display device 21 is a display unit that displays an endoscopic image on the basis of an image-acquisition signal acquired by the endoscope 1 and is formed of, for example, an LCD panel or the like.

The control processor 19 transmits a control signal, various detection signals, an acquired image signal, etc. through the signal cable penetrating through the endoscope 1. Then, the control processor 19 transfers a processed image signal to the display device 21 and causes the display device 21 to display an endoscopic image, various types of information, etc. Furthermore, illumination light from the light source device 20 is guided, via the connector part 5, the universal cord 4, and the operation part 3, to the illumination optical system 30, which is disposed in the insertion portion 2, and is radiated onto a nearby observation target.

Figure 5:
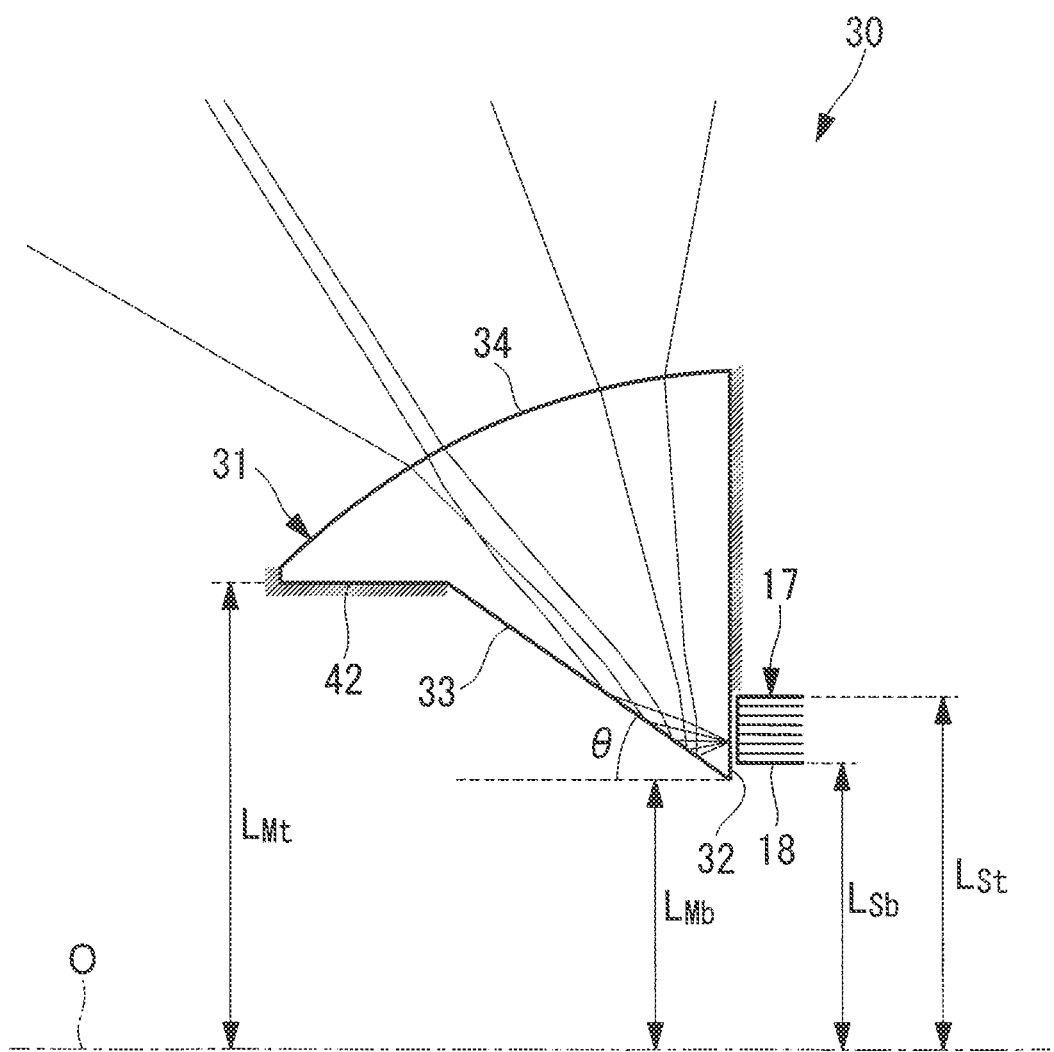
FIG. 5 is a longitudinal sectional view showing the illumination optical system according to this embodiment, which is provided in the endoscope shown in FIG. 1.

As shown in FIGS. 4 and 5, the illumination optical system 30 of this embodiment is provided with a diffusion element 31 as the illumination lens 12.

The diffusion element 31 is formed, at a radially outer side of the image-capturing optical system 14, into an annular shape disposed so as to surround the image-capturing optical system 14 over a predetermined circumferential region centered on an optical axis (center axis) O of the image-capturing optical system 14.

Furthermore, the diffusion element 31 is provided with: an incident surface 32 from which illumination light guided in the insertion portion 2 by the light guide 17 is made to enter; a reflecting surface (deflection surface) 33 that deflects, through reflection, the illumination light that has entered from the incident surface 32; and an emission surface 34 from which the illumination light deflected at the reflecting surface 33 is emitted radially outward and forward.

The incident surface 32 is formed of a flat surface extending, at the base end of the diffusion element 31, so as to be perpendicular to the optical axis O.

The reflecting surface 33 has a tapered shape that is inclined radially outward in the direction toward the distal end. The tip of the reflecting surface 33 extends forward, in a flat (cylindrical) manner, substantially along the optical axis O.

Furthermore, the emission surface 34 is disposed at a radially outer side of the reflecting surface 33, and at least a part thereof is formed of a curved surface inclined so as to approach the optical axis O in the direction toward the distal end. The emission surface 34 extends forward beyond the distal end of the reflecting surface 33 and is connected to a flat section 42 that extends forward from the reflecting surface 33.

An incident area through which illumination light is made to enter the diffusion element 31 from the light guide 17 is disposed at a radially inner section of the incident surface 32, and the reflecting surface 33 is disposed at a position opposed to the incident surface 32 in the direction of the optical axis O. Specifically, in FIG. 5, the following conditional expressions are satisfied.

$$L_{Mb} \leq L_{Sb} < L_{Mt}$$

$$L_{Mb} \leq L_{St} < L_{Mt}$$

where $L_{Mb}$ is the minimum radius size of the reflecting surface 33, $L_{Mt}$ is the maximum radius size of the reflecting surface 33, $L_{Sb}$ is the minimum radius size of the incident area, and $L_{St}$ is the maximum radius size of the incident area.

Accordingly, the reflecting surface 33 is disposed in such a region as to reflect and deflect most of the illumination light entering the diffusion element 31 through the incident area.

An inclination angle θ of the reflecting surface 33 with respect to the optical axis O is set to 0<θ≤45°, desirably, 20°≤θ≤45°. Accordingly, most of the illumination light that enters the diffusion element 31 from the incident area and that is incident on the reflecting surface 33 can be directed radially outward and obliquely forward. The emission surface 34 is inclined so as to cause most of the illumination light deflected by the reflecting surface 33 to be incident thereon at an angle close to 90°. Accordingly, it is possible to suppress total reflection of the illumination light at the emission surface 34, thus making it possible to improve the light utilization efficiency.

In FIG. 5, hatched areas may be fixed, via an adhesive agent, to frame bodies 15a and 15b that support the diffusion element 31, thus using the hatched areas as absorbing surfaces that absorb illumination light, or may be subjected to metal coating, thus using the hatched areas as reflecting surfaces.

Figure 17:
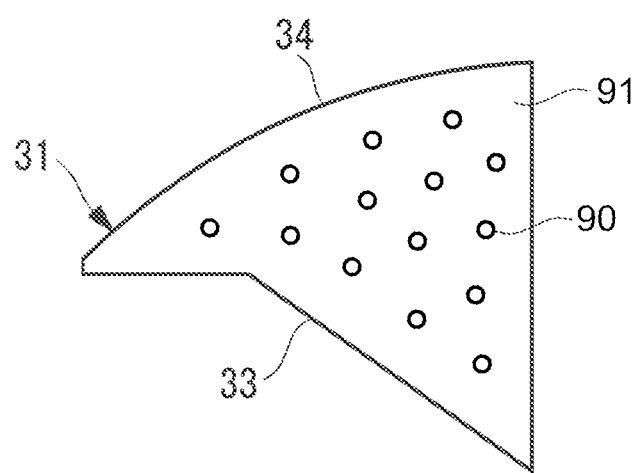
FIG. 17 is a longitudinal sectional view schematically showing the diffusion element of the illumination optical system shown in FIG. 5.

The diffusion element 31 is formed by dispersing fine particles 90 of at least one kind in an optically transparent resin material 91 (homogeneous medium, resin). See FIG. 17. The fine particles diffuse illumination light due to Mie scattering.

In the diffusion element 31, a scattering coefficient μs and an anisotropy parameter g in the Mie scattering theory satisfy the following conditional expressions.

$$0.06 \leq \mu s (1/mm) \leq 20 \quad (1)$$

$$0.5 \leq g < 1 \quad (2)$$

By satisfying these conditional expressions, it is possible to sufficiently reduce the diffusivity of the diffusion element 31, to gradually expand illumination light through scattering, to reduce backscattering, and to sufficiently reduce the components of illumination light that return toward the light guide 17.

More specifically, the diffusion element 31 satisfies the following conditional expressions.

$$0.005 \leq |n1-n2| \leq 0.5 \quad (3)$$

$$0.5 \leq d(\mu m) \leq 50 \quad (4)$$

$$0.1 \leq c(\text{weight }\%) \leq 50 \quad (5)$$

where n1 is the refractive index of the resin material, n2 is the refractive index of the fine particles of at least one kind, d is the particle size of the fine particles, and c is the mass concentration of the fine particles with respect to the resin material.

By forming the diffusion element 31 using such materials, it is possible to realize the diffusion coefficient in Conditional Expression (1) and the anisotropy parameter in Conditional Expression (2).

Note that, it is preferred that the above Conditional Expressions be:

$$0.01 \leq |n1-n2| \leq 0.5 \quad (3');$$

$$0.5 \leq d(\mu m) \leq 30 \quad (4'); \text{ and}$$

$$0.1 \leq c(\text{weight }\%) \leq 20 \quad (5').$$

As the fine particles, it is possible to adopt inorganic fine particles, such as particles of silica, alumina, talc, zirconia, zinc oxide, or titanium dioxide, or to adopt organic fine particles, such as particles of polymethyl methacrylate resin, polystyrene resin, polyurethane resin, benzoguanamine resin, or silicone resin. Furthermore, air bubbles may also be adopted as the fine particles.

Furthermore, as the resin material, it is possible to use polyester-based resin, acrylic-based resin, acrylic urethane-based resin, polyester acrylate-based resin, polyurethane acrylate-based resin, epoxy acrylate-based resin, urethane-based resin, epoxy-based resin, polycarbonate-based resin, cellulose-based resin, acetal-based resin, vinyl-based resin, polyethylene-based resin, polystyrene-based resin, polypropylene-based resin, polyamide-based resin, melamine-based resin, phenolic-based resin, silicon-based resin, or fluorine-based resin. If used as the outermost layer of the endoscope 1, which is inserted into a human body, it is preferred to adopt cycloolefin-based resin or sulfonic acid-based resin from the perspective of biocompatibility, chemical resistance, etc.

Figure 6:
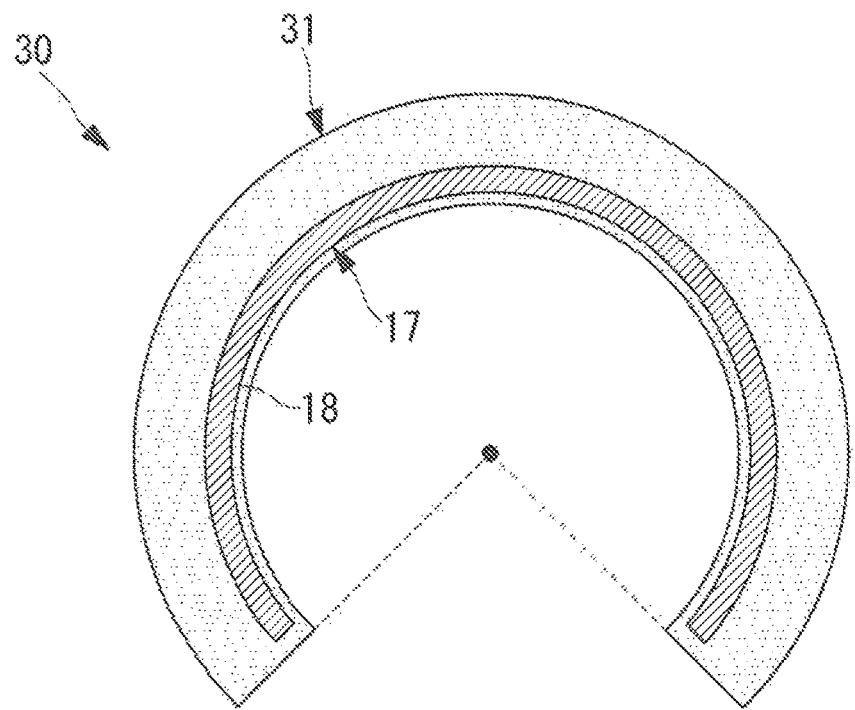
FIG. 6 is a transverse sectional view showing an example positional relationship between a diffusion element and a light guide in the illumination optical system shown in FIG. 5.
Figure 7:
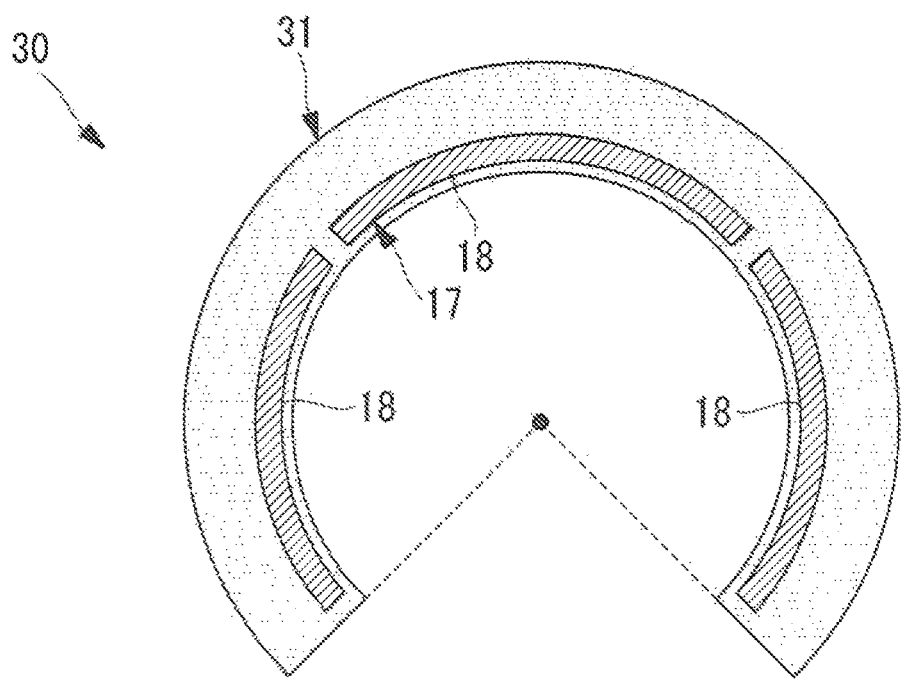
FIG. 7 is a transverse sectional view showing another example positional relationship between the diffusion element and the light guide in the illumination optical system shown in FIG. 5.
Figure 16:
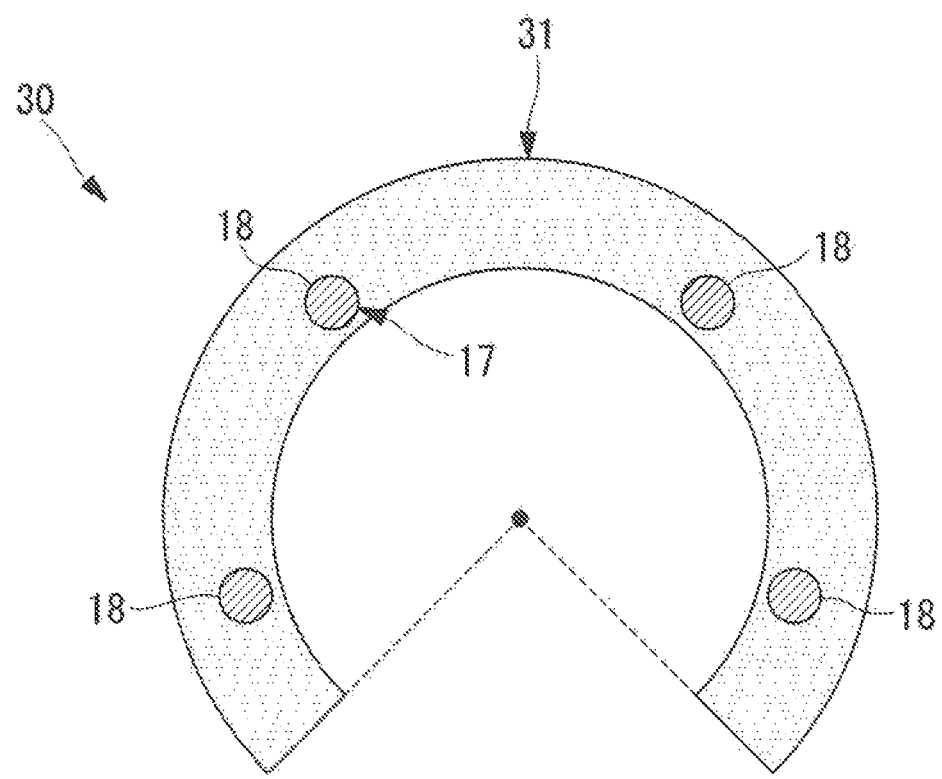
FIG. 16 is a transverse sectional view showing an example positional relationship between the diffusion element and the light guide in an eighth modification of the illumination optical system shown in FIG. 5.

It is preferred that the light guide 17 be formed into an annular shape extending in the circumferential direction of the incident surface 32 of the diffusion element 31. As shown in FIG. 6, for example, this can be formed by forming an emission end of the fiber bundle 18, which guides illumination light from the light source device 20, into the annular shape. Instead of this, as shown in FIGS. 7 and 16, it is also possible to divide the fiber bundle 18 into a plurality of parts in the circumferential direction and to make illumination light enter a plurality of areas corresponding thereto. In FIG. 7, the light guide 17 is composed of three fiber bundles 18 that are respectively formed into shapes serving as parts of a circular arc, and the respective fiber bundles are disposed, at intervals, in three areas into which the diffusion element 31 is equally divided. In FIG. 16, the light guide 17 is composed of four fiber bundles 18 each having a substantially circular emission surface, and the respective fiber bundles 18 are disposed, at intervals, in four areas into which the diffusion element 31 is equally divided.

The operation of the thus-configured illumination optical system 30 of this embodiment will be described below.

According to the illumination optical system 30 of this embodiment, when illumination light guided by the light guide 17 is incident on the incident surface 32 of the diffusion element 31, while traveling in the diffusion element 31, part of the illumination light collides with the fine particles, thus being scattered.

In this case, because the illumination optical system 30 of this embodiment satisfies Conditional Expressions (1) and (2), it is possible to sufficiently reduce the diffusivity of the diffusion element 31, to gradually expand the traveling direction of the illumination light through scattering, to reduce backscattering at the fine particles, and to sufficiently reduce the components of the illumination light returning toward the light source device 20. As a result, there is an advantage in that it is possible to perform uniform illumination over a wide region by using illumination light emitted from the emission surface 34 and to improve illumination-light utilization efficiency by reducing loss of illumination light in the diffusion element 31.

Figure 13:
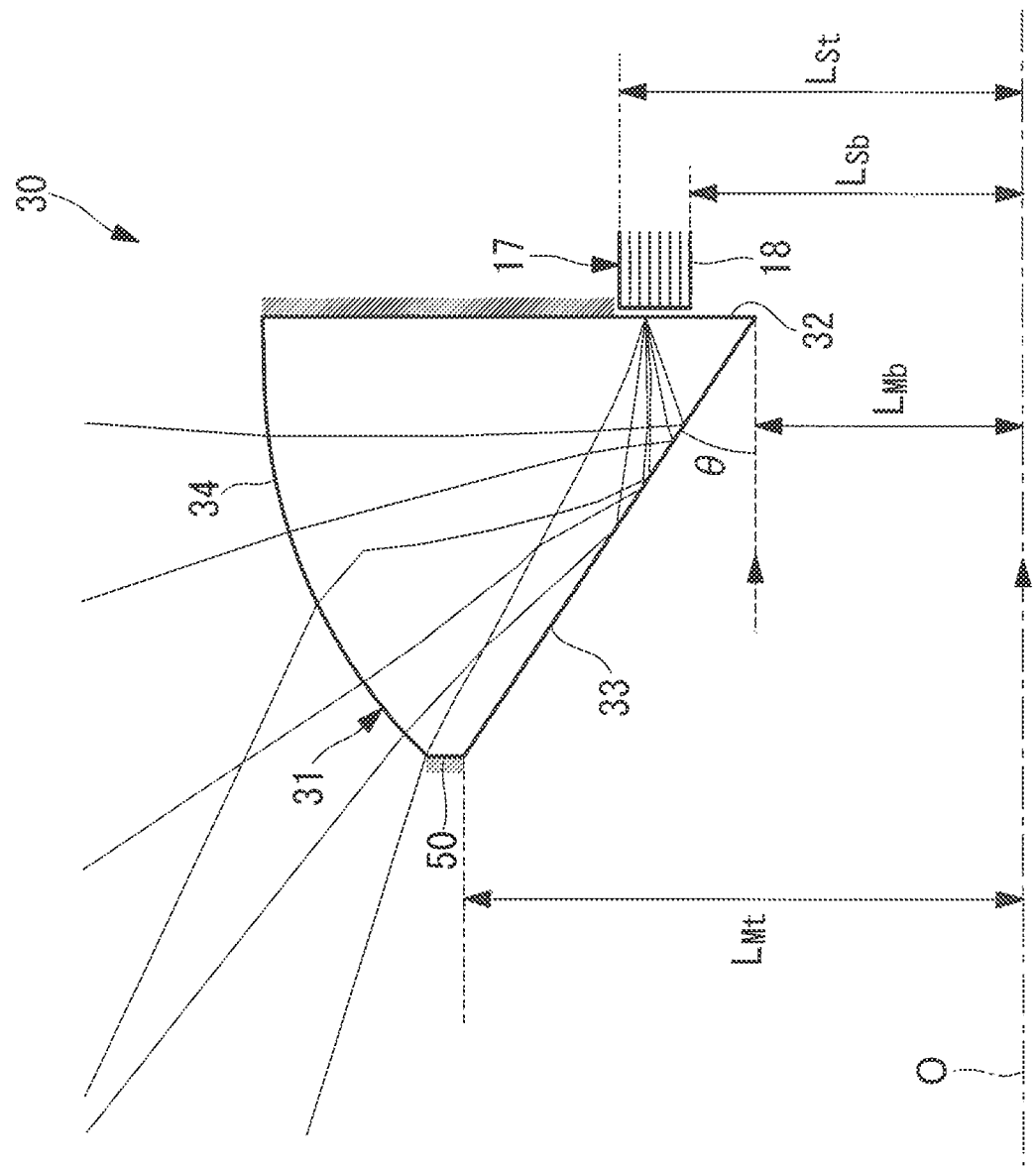
FIG. 13 is a longitudinal sectional view showing a fifth modification of the illumination optical system shown in FIG. 5.

FIG. 13 is a view showing another example of the diffusion element 31. This diffusion element 31 is provided with a flat surface 50 that rises from the distal end of the reflecting surface 33 so as to be substantially parallel to the incident surface 32, and the terminal ends of the flat surface 50 and the reflecting surface 33 are connected to each other. The flat surface 50 can be used for adhering or fixing the diffusion element 31.

Figure 14:
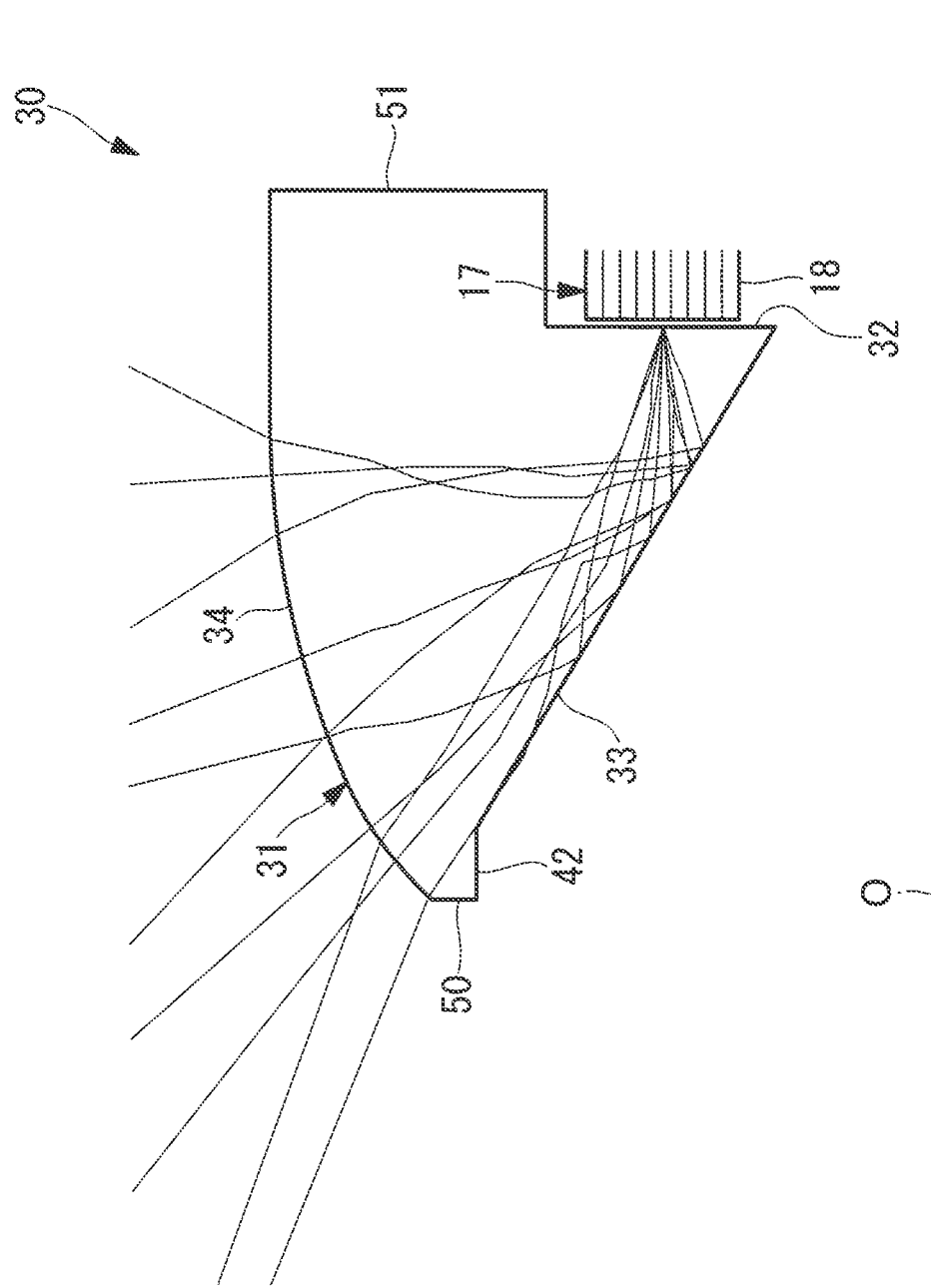
FIG. 14 is a longitudinal sectional view showing a sixth modification of the illumination optical system shown in FIG. 5.

FIG. 14 is a view showing still another example of the diffusion element 31. This diffusion element 31 has a protruding section 51 that protrudes rearward from the incident surface 32, at an outer side of the flat incident surface 32, whose rear surface is opposed to the light guide 17 and which receives light, and a rear surface 52 of the protruding section 51 and the emission surface 34 are connected to each other.

With this structure, because the terminal end of the emission surface 34 close to the light source device 20 is positioned closer to the rear side than the light-emitting surface of the light source device 20 is, an effective area of the emission surface 34 expands rearward, thus making it possible to expand an illumination area farther toward the rear side.

Figure 15:
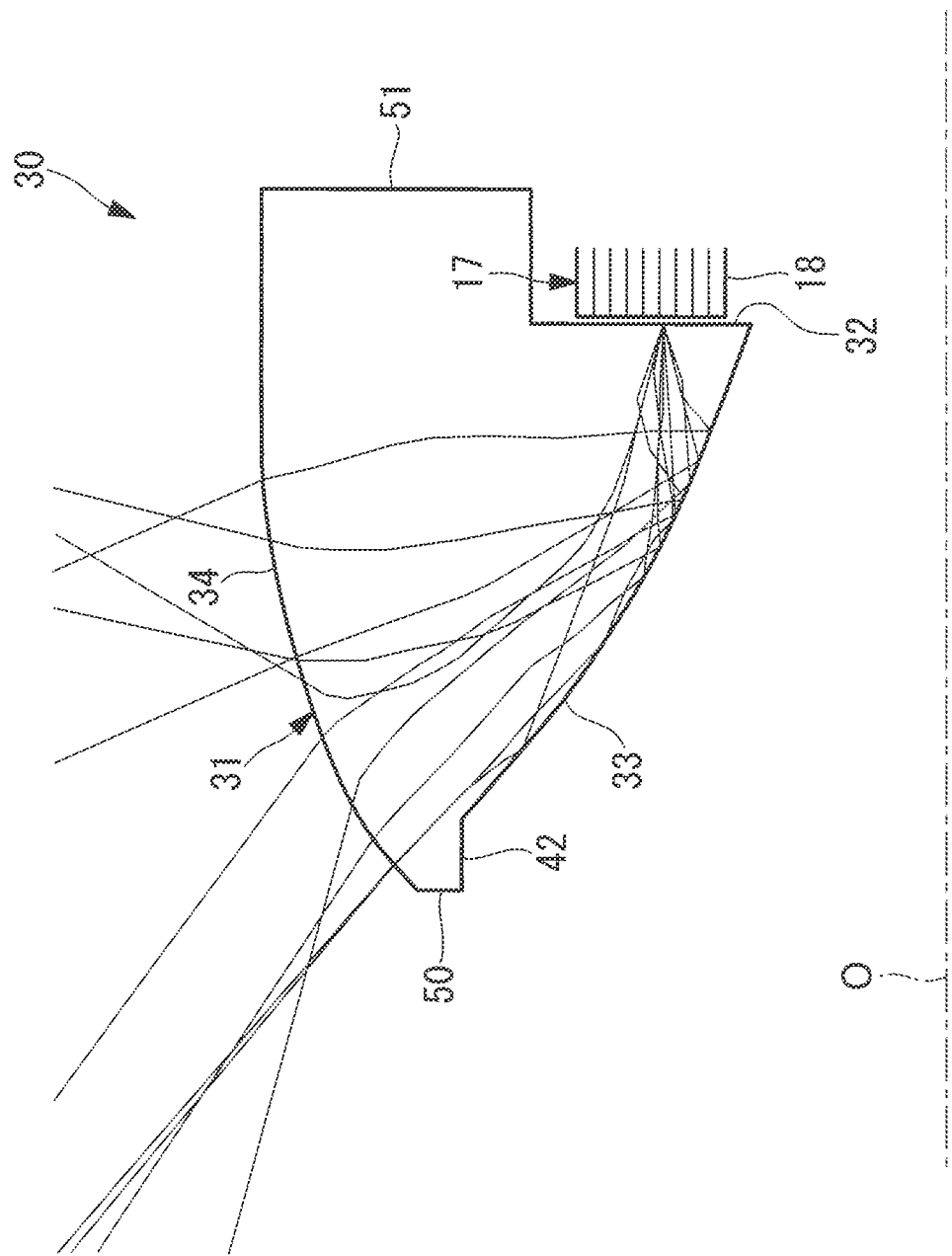
FIG. 15 is a longitudinal sectional view showing a seventh modification of the illumination optical system shown in FIG. 5.

Note that, in each of the diffusion elements 31, although the reflecting surface 33 is formed flat in cross section, it is also possible to form the reflecting surface 33 into a shape having a curvature, such as a concave surface or a convex surface. By doing so, the reflecting surface 33 shows a convergence and divergence effect, and the convergence and divergence effect can be used for control of the distribution of illumination light. FIG. 15 shows an example in which the reflecting surface 33 is formed in a protruding surface, in the example shown in FIG. 14.

Figure 8:
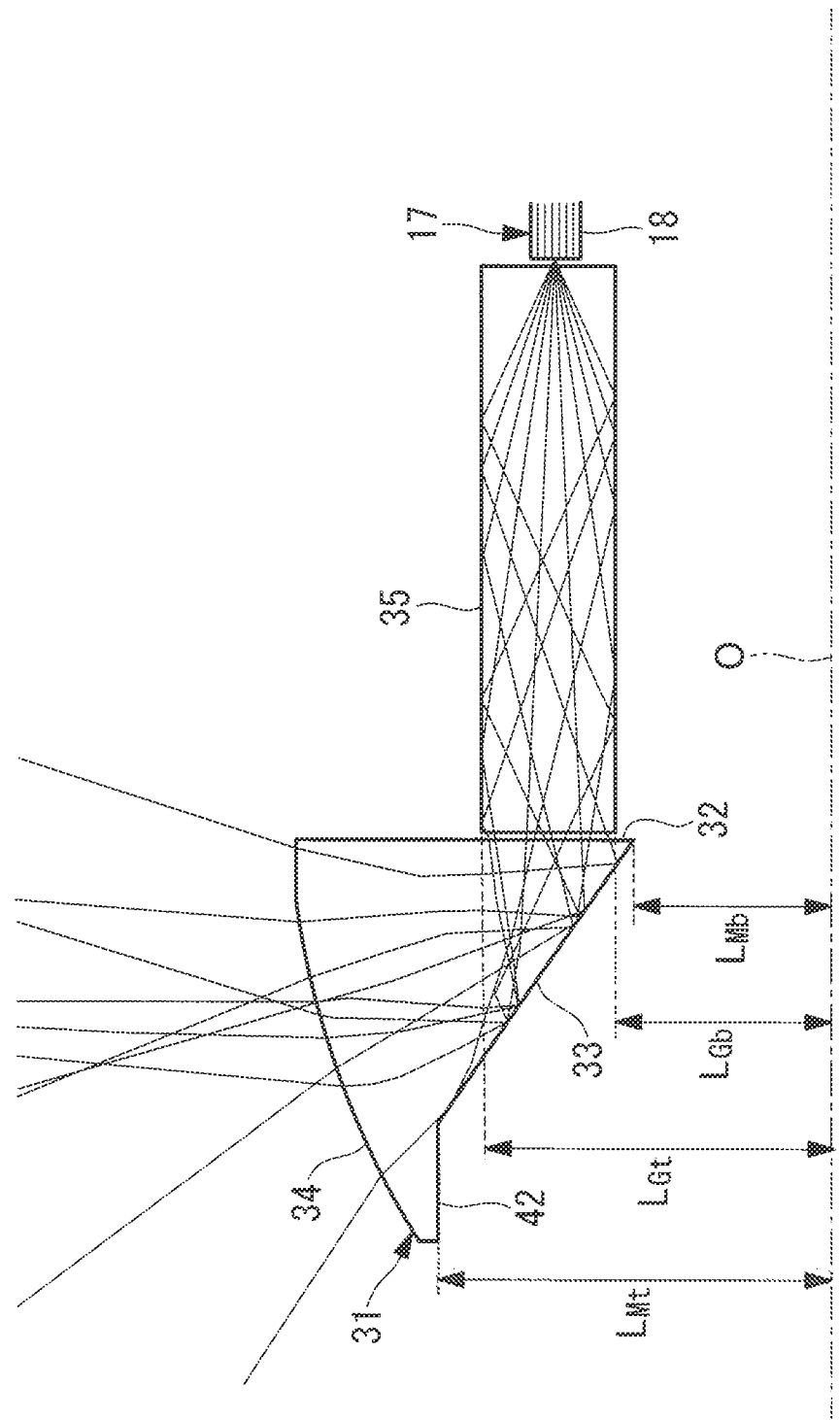
FIG. 8 is a longitudinal sectional view showing a first modification of the illumination optical system shown in FIG. 5.

Returning to the example shown in FIG. 5, in this embodiment, as shown in FIG. 8, it is also possible to provide, between the light guide 17 and the diffusion element 31, a waveguide member 35 that guides, through total internal reflection, illumination light emitted by the light guide 17 and that causes the illumination light to be incident on the incident surface 32 of the diffusion element 31. Furthermore, in FIG. 8, it is preferred that the following Conditional Expressions be satisfied:

$$L_{Mb} \leq L_{Gb} < L_{Mt}; \text{ and}$$

$$L_{Mb} \leq L_{Gt} < L_{Mt},$$

where $L_{Gb}$ is the minimum radius size of the waveguide member 35, and $L_{Gt}$ is the maximum radius size of the waveguide member 35.

The waveguide member 35 is formed into a cylindrical shape extending coaxially with the diffusion element 31 and over a circumferential region equivalent to that of the diffusion element 31, and causes illumination light that has entered from the emission end of the light guide 17, which is disposed so as to be opposed to an end surface of the waveguide member 35 close to the base end, to travel in the longitudinal direction while expanding in the circumferential direction, thus making it possible to cause illumination light that is uniform over the entire circumference to enter the diffusion element 31.

Figure 9:
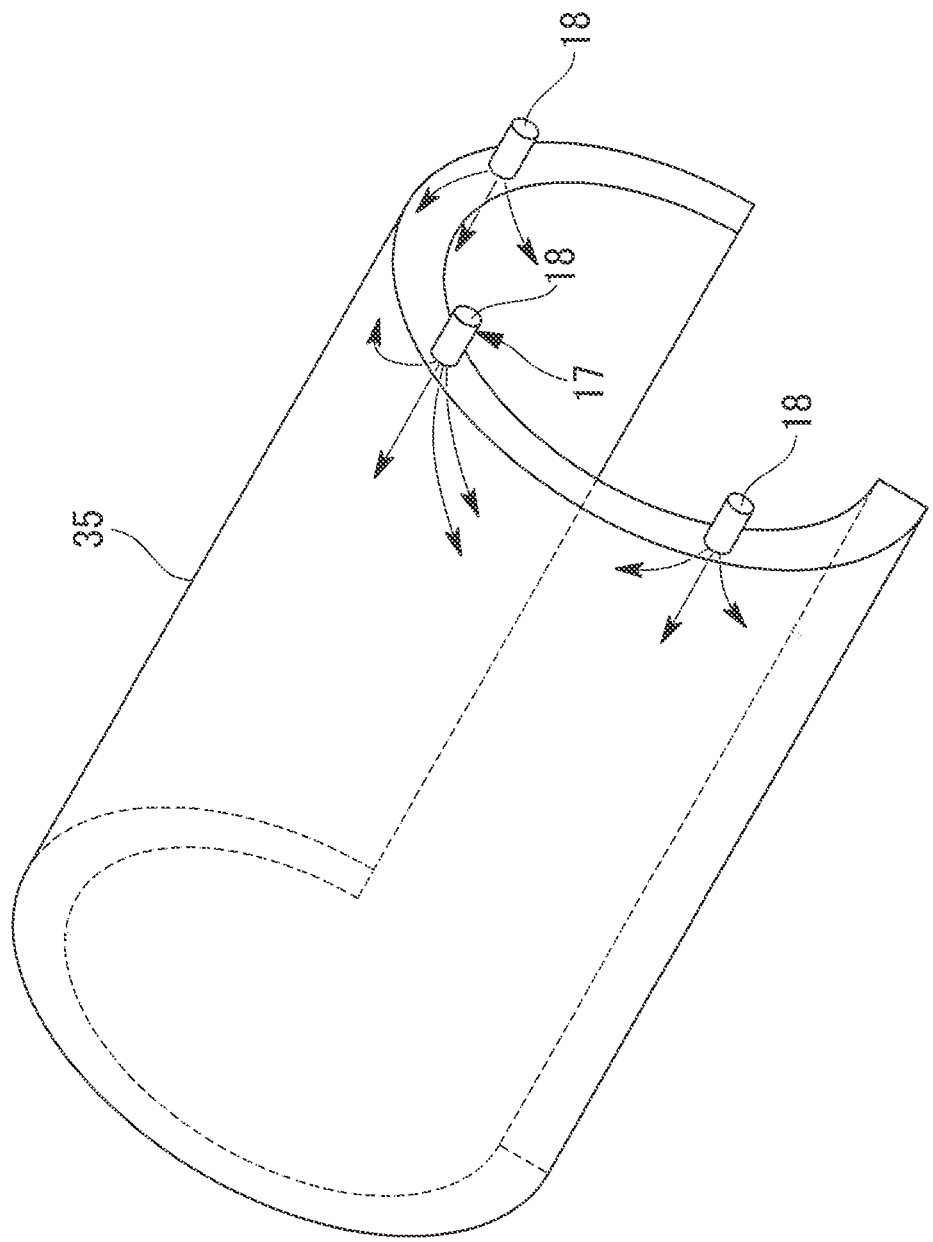
FIG. 9 is a perspective view showing an example arrangement of a waveguide member and a light guide that are provided in the illumination optical system shown in FIG. 6.

In particular, as shown in FIG. 9, in a case in which the fiber bundles 18, which constitute the light guide 17, are disposed at intervals in the circumferential direction in a discontinuous manner, the waveguide member 35 can expand illumination light in the circumferential direction and can cause illumination light that is uniform over the entire circumference to enter the diffusion element 31.

Furthermore, by forming the waveguide member 35 by using a resin material that is optically transparent and fine particles that are dispersed in the resin material, it is also possible to make the waveguide member 35 have diffusion properties. By doing so, illumination light is scattered also in the waveguide member 35, thus making it possible to cause more uniform illumination light to enter the diffusion element 31.

Furthermore, the waveguide member 35 may also be formed into a tapered shape expanding or a tapered shape narrowing along the longitudinal axis. By forming the waveguide member 35 into a tapered shape expanding in the traveling direction of illumination light, it is possible to reduce the NA of the illumination light and to cause the illumination light to enter the diffusion element 31. Furthermore, By forming the waveguide member 35 into a tapered shape expanding in the traveling direction of illumination light, it is possible to increase the NA of the illumination light and to cause the illumination light to enter the diffusion element 31.

教 Furthermore, the diffusion element 31 and the waveguide member 35 can be disposed with a gap therebetween or can be adhered to each other with a transparent adhesive agent. By adhesion with a transparent adhesive agent, there is an advantage in that Fresnel loss on the boundary surface is reduced, thus making it possible to further improve the illumination-light utilization efficiency. Furthermore, the diffusion element 31 and the waveguide member 35 may also be integrally formed through two-color molding.

Figure 10:
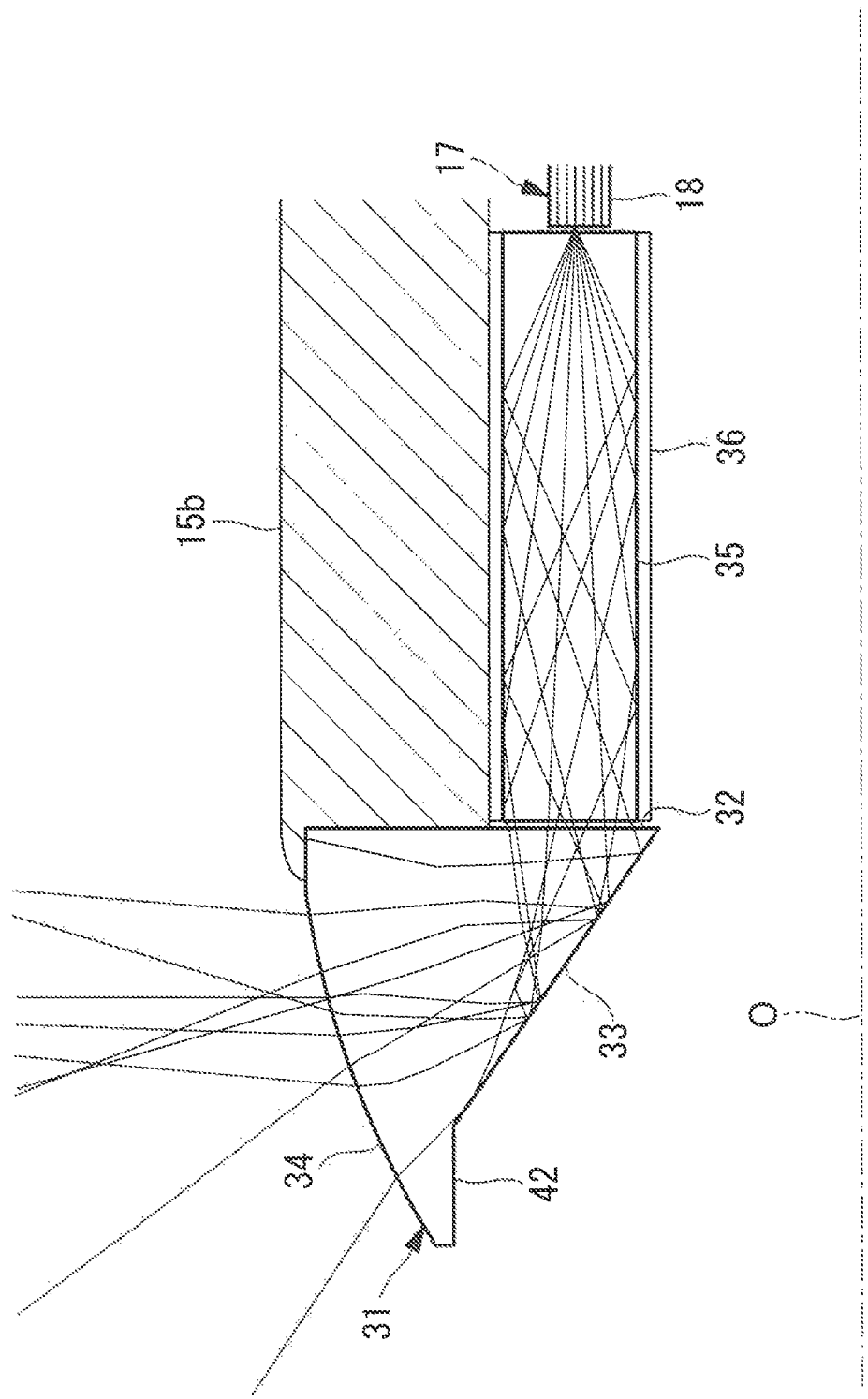
FIG. 10 is a longitudinal sectional view showing a second modification of the illumination optical system shown in FIG. 5.

Furthermore, in order to achieve total reflection conditions on an inner surface of the waveguide member 35, as shown in FIG. 10, a clad material 36 having a low refractive index, such as fluororesin, may also be coated on the inner surface and an outer surface of the waveguide member 35. Accordingly, the waveguide member 35 can be adhesively fixed to the frame body 15b etc. thus making it possible to facilitate manufacturing. The clad material 36 may also be formed of an adhesive agent, and fixing of the waveguide member 35 to the frame body 15b may be performed by means of the clad material 36.

Furthermore, the diffusion element 31 and the waveguide member 35 may be integrally formed by using the same diffusion material.

Figure 11:
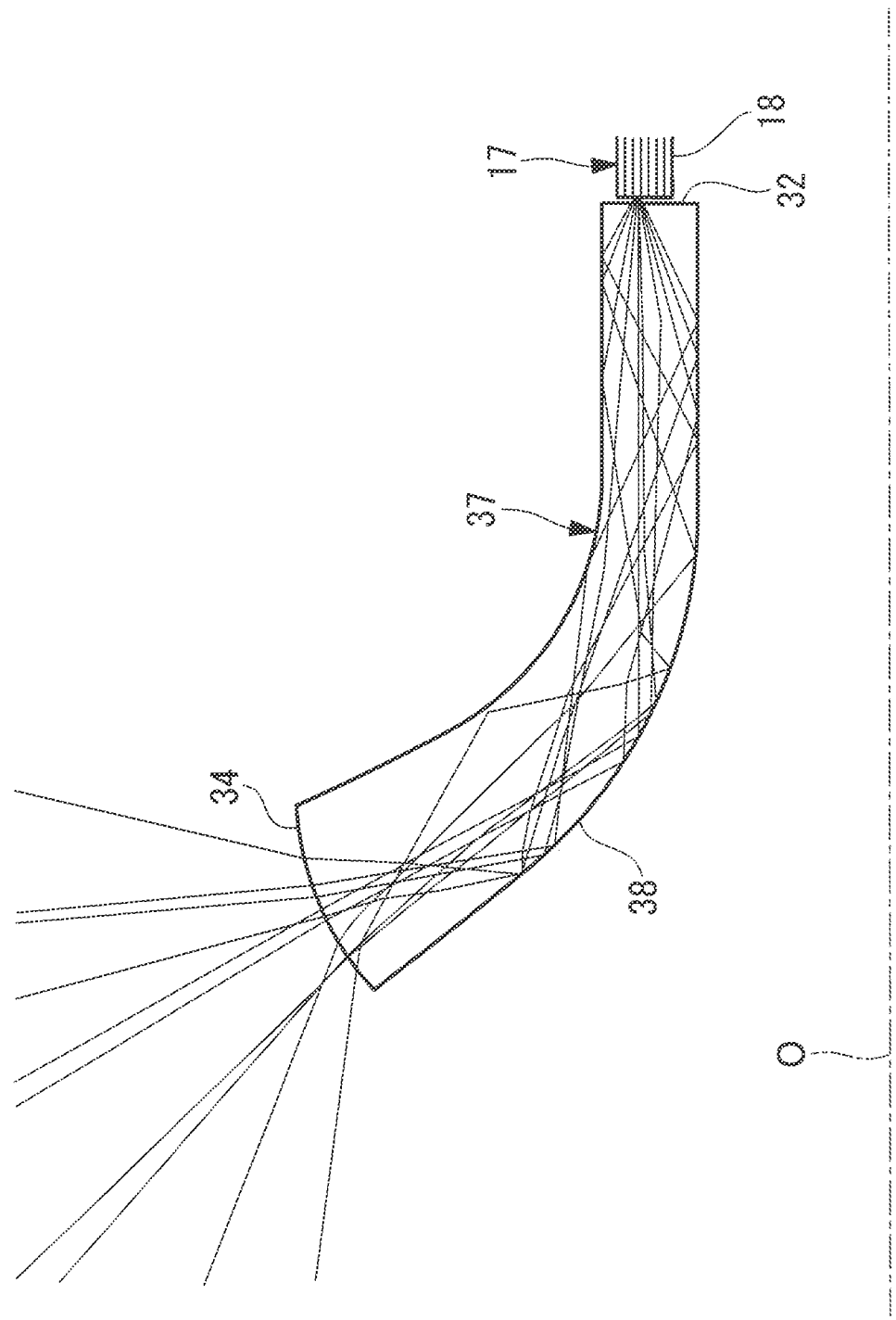
FIG. 11 is a longitudinal sectional view showing a third modification of the illumination optical system shown in FIG. 5.

In this case, as shown in FIG. 11, it is also possible to adopt a diffusion element 37 having a shape in which a distal end of a cylinder-shaped section extending along the optical axis O is curved toward a radially outer side and is expanded.

By doing so, there is an advantage in that it is possible to form, instead of the reflecting surface 33, a deflection surface 38 that deflects illumination light through total internal reflection and to perform highly-efficient illumination by reducing illumination-light attenuation caused through reflection.

Furthermore, by adopting a longitudinal cross sectional shape expanding toward the emission surface 34, there is an advantage in that light guide efficiency can be improved by suppressing excessive spreading of illumination light spread by the fine particles.

Figure 12:
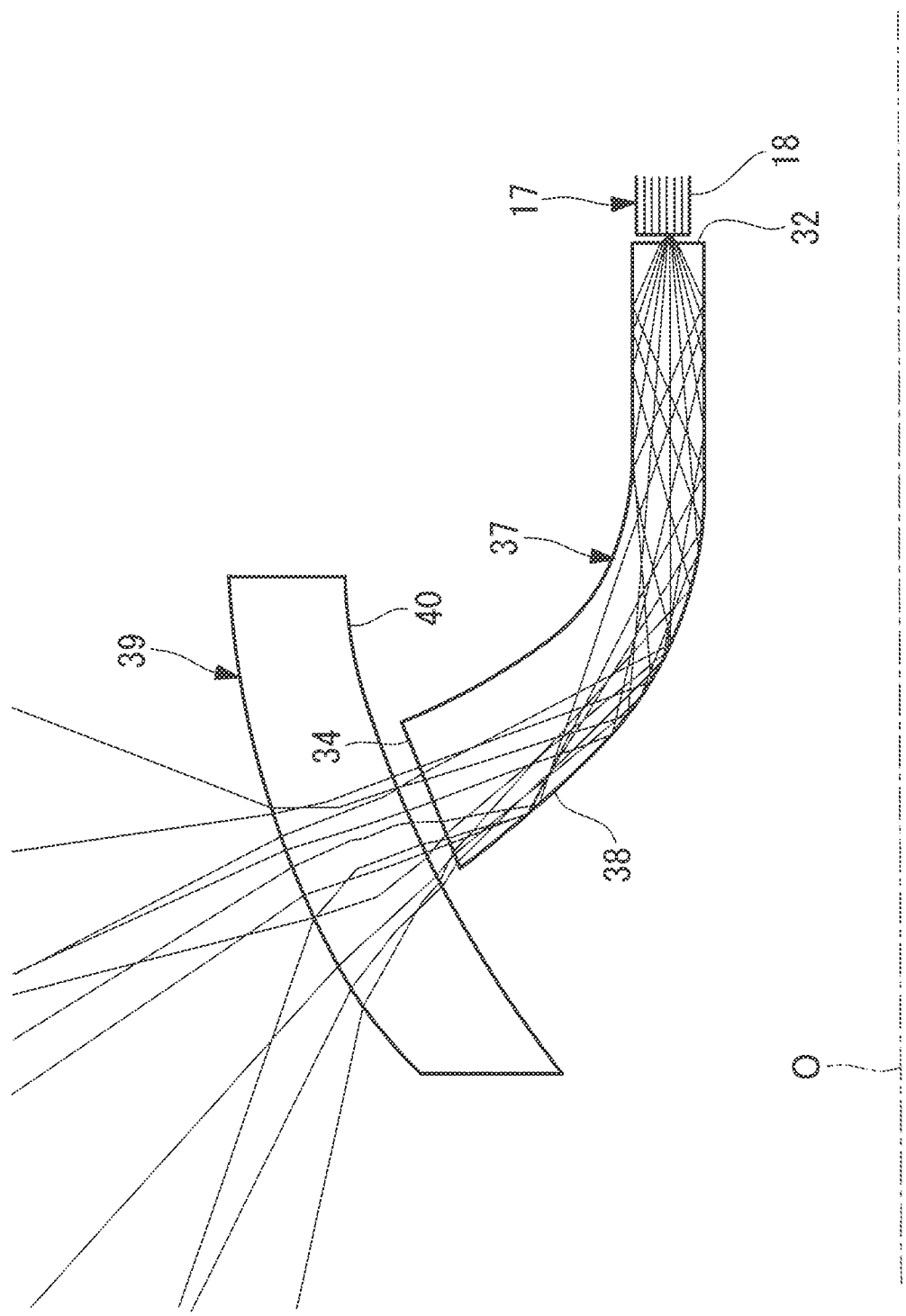
FIG. 12 is a longitudinal sectional view showing a fourth modification of the illumination optical system shown in FIG. 5.

FIG. 12 shows an example in which the diffusion element 31 is composed of two parts, i.e., an outer diffusion part 39 that has only a diffusion function and a waveguide part 37 that has a deflection function. In the figure, reference sign 40 denotes an incident surface of the outer diffusion part 39. By making the diffusivities of the two parts different from each other, there is an advantage in that, in a case in which the sizes of the fiber bundles 18 of the light guide 17 are small, as shown in FIG. 16, it is possible to easily obtain a design for achieving both equalization of illumination light in the circumferential direction and improvement of the illumination-light utilization efficiency. Furthermore, the waveguide part 37 may also be formed of a transparent light-guide member, without dispersing fine particles therein. In this case, as the waveguide part 37, the light guide 17 of the light source device 20 may also be formed into a shape curved outward and be directly used. By using a plastic fiber as the light guide 17, loss of light amount caused by being curved can be reduced, thus making it possible to improve the utilization efficiency.

Furthermore, in a case in which the outer diffusion part 39 and the waveguide part 37 both have a diffusion function, it is preferred that the outer diffusion part 39 and the waveguide part 37 both satisfy Conditional Expressions (1) and (2). Furthermore, it is further preferred that Conditional Expressions (3), (4), and (5) be satisfied.

Furthermore, although a description has been given of an example case in which illumination light from the light source device 20 is guided by using the light guide 17, instead of this, it is also possible to cause illumination light from an LED or a laser light source to directly enter the diffusion element 31 or the waveguide member 35.

Note that, although the scattering coefficient and the anisotropy parameter used in the present invention are generally used, a brief explanation thereof will be given below just in case. (Reference literature: "Absorption and Scattering of Light by Small Particles", Craig F. Bohren and Donald R. Huffman, Wiley-VCH Verlag GmbH & Co. KGaA)

The scattering coefficient μs of the diffusion element 31 can be expressed by the following Expression (6) when the scatter cross section of the fine particles is set as $\sigma_s$, and the number density of the fine particles dispersed in the diffusion element 31 is set as $\rho_s$.

$$\mu s = \rho_s \sigma_s \quad (6)$$

$\sigma_s$ in Expression (6) can be expressed by the following Expression (7) when the geometric cross section of the fine particles is set as A, and the scattering efficiency of the fine particles is set as $Q_s$.

$$\sigma_s = Q_s A \quad (7)$$

$\sigma_s$ in Expression (7) is expressed by the following Expression (8).

$$Q_S = \frac{2}{x^2} \sum_{k=1}^{\infty} (2k+1)(|a_k|^2 + |b_k|^2) \quad \text{where} \quad (8)$$

$$a_k = \frac{n^2 j_k(nx)[xj_k(x)]' - j_k(x)[kxj_k(nx)]'}{n^2 j_k(nx)\left[xh_k^{(1)}(x)\right]' - h_k^{(1)}(x)[nxj_k(nx)]'} \quad (9)$$

$$b_k = \frac{j_k(nx)[xj_k(x)]' - j_k(x)[nxj_k(nx)]'}{j_k(nx)\left[xh_k^{(1)}(x)\right]' - h_k^{(1)}(x)[nxj_k(nx)]'} \quad (10)$$

$$h_k^{(1)} = j_k(z) + i y_k(z) \quad (11)$$

$$j_k(z) = \sqrt{\frac{\pi}{2z}} J_{k+0.5}(z) \quad (12)$$

$$y_k(z) = \sqrt{\frac{\pi}{2z}} Y_{k+0.5}(z) \quad (13)$$

$J_{k+0.5}(z)$ in Expression (12) and $Y_{k+0.5}(z)$ in Expression (13) are a Bessel function of the first kind and a Bessel function of the second kind, respectively. Note that, i is an imaginary unit.

Furthermore, n indicates the ratio of the refractive index of the fine particles to the refractive index of the transparent resin and is expressed by the following Expression (14).

$$n = \frac{n_2}{n_1} \quad (14)$$

x indicates the ratio of the radius a of each of the fine particles to the wavelength λ of illumination light and is expressed by the following Expression (15).

$$x = 2\pi \frac{a}{\lambda} \quad (15)$$

The anisotropy parameter g of the fine particles means the average of cosines of scattering angles when light is scattered by a single particle, and can take a value satisfying $-1 \le g \le 1$. In particular, when g=−1, light is scattered only in the opposite direction from the incident angle, and, when g=1, light is scattered only in the same direction as the incident angle (i.e., light is not scattered). Furthermore, when g=0, perfect isotropic scattering is provided. g is calculated by the following Expression (16).

$$Q_S \cdot g = \frac{4}{x^2} \left[ \sum_{k=1}^{\infty} \frac{k(k+2)}{k+1} \mathrm{Re}\{a_k a_{k+1}^* + b_k b_{k+1}^*\} + \sum_{k=1}^{\infty} \frac{2k+1}{k(k+1)} \mathrm{Re}\{a_k b_k^*\} \right] \quad (16)$$

Note that, * in Expression (16) denotes a complex conjugate, and Re indicates the real part in { }.

As a result, the above-described embodiment leads to the following aspect.

One aspect of the present invention provides an illumination optical system including a diffusion element that diffuses illumination light entering from a light source, the diffusion element emitting the illumination light, wherein the diffusion element is formed by dispersing fine particles of at least one kind in a homogeneous medium that is made of a material different from the fine particles and satisfies the following conditional expressions:

$$0.06 \le \mu s (1/\mathrm{mm}) \le 20; \text{ and}$$

$$0.5 \le g < 1,$$

where μs is a scattering coefficient of the diffusion element, and g is an anisotropy parameter of the fine particles in the homogeneous medium.

According to this aspect, when illumination light emitted by the light source enters the diffusion element, while being guided in the homogeneous medium, the illumination light is scattered through collision with the fine particles dispersed in the homogeneous medium. By setting the anisotropy parameter of the fine particles so as to satisfy $0.5 \le g < 1$, the scattering angle at single collision with a particle is reduced, thus making it possible to prevent the direction of the illumination light from being significantly changed by single scattering and to suppress backscattering. Furthermore, by setting the scattering coefficient of the diffusion element so as to satisfy $0.06 \le \mu s \le 20$, opportunities for the illumination light to collide with the fine particles are limited, and many components of the illumination light travel in the diffusion element without being strongly scattered. Accordingly, the components of illumination light returning toward the light source are reduced, thus making it possible to improve the illumination-light utilization efficiency.

In the above-described aspect, the homogeneous medium may be an optically transparent resin and may satisfy the following conditional expressions:

$$0.005 \leq |n1-n2| \leq 0.5;$$

$$0.5 \leq d(\mu m) \leq 50; \text{ and}$$

$$0.1 \leq c(\text{weight \%}) \leq 50,$$

where n1 is a refractive index of the resin, n2 is a refractive index of the fine particles of at least one kind, d is a particle size of the fine particles, and c is a mass concentration of the fine particles with respect to the resin.

Furthermore, in the above-described aspect, the diffusion element may be provided with: an incident surface that is formed into an annular shape extending over the entire circumference or partly in the circumferential direction about a center axis, that is disposed at one end thereof in the direction of the center axis, and on which the illumination light from the light source is incident; a deflection surface that is disposed so as to be opposed to the incident surface in the direction of the center axis and that is inclined so as to extend toward a radially outer side, as the distance from the incident surface increases along the center axis, at an angle greater than 0° and equal to or less than 45° with respect to the center axis, and so as to deflect the illumination light incident on the incident surface toward a radially outer side; and an emission surface that is disposed closer to a radially outer side than the deflection surface is and from which the illumination light deflected at the deflection surface is emitted; and the emission surface may be inclined so as to extend radially inward as the distance from the incident surface increases along the center axis.

Although the illumination light emitted by the light source and entering the diffusion element from the incident surface is scattered by the fine particles in the diffusion element, most of the illumination light travels in the diffusion element without being strongly diffused as in isotropic scattering, is deflected radially outward by the deflection surface, which is opposed to the incident surface in the center-axis direction, and is directed to the emission surface. Then, while traveling from the deflection surface to the emission surface, the illumination light is not so strongly diffused in the same way. Thus, most of the illumination light travels to the emission surface without being backscattered on the way to the emission surface, and the components that are totally reflected at the emission surface are reduced. Thus, the components of the illumination light returning toward the light source are reduced, thus making it possible to improve the illumination-light utilization efficiency and to obtain uniform illumination in a wide region.

Furthermore, in the above-described aspect, the deflection surface may have a curvature.

Furthermore, the above-described aspect may further include, between the light source and the incident surface, a waveguide member that is formed into an annular shape extending over the entire circumference or partly in the circumferential direction about the center axis, that guides, through total internal reflection, the illumination light emitted by the light source, and that causes the illumination light to be incident on the incident surface.

By doing so, because illumination light emitted by the light source uniformly expands over the entire circumferential direction while being guided in the waveguide member, even in a case in which the light source is discontinuously disposed at intervals in the circumferential direction, uniform illumination light can be emitted from the entire emission surface of the diffusion element.

Furthermore, in the above-described aspect, the waveguide member may be formed as a light diffusion element by dispersing fine particles of at least one kind in an optically transparent resin.

By doing so, because the illumination light is guided while being scattered by the fine particles dispersed in the transparent resin, which constitutes the waveguide member, more uniform illumination can be performed.

Furthermore, in the above-described aspect, the deflection surface may deflect the illumination light through total internal reflection.

By doing so, deflection caused by reflection is eliminated, thus suppressing attenuation of the illumination light and making it possible to perform more efficient illumination.

Furthermore, in the above-described aspect, the diffusion element may be formed as a waveguide having an annular shape extending over the entire circumference or partly in the circumferential direction about the center axis, and a transverse cross section of the diffusion element may have a shape curved outward with respect to the center axis, from an incident surface toward an emission surface; and the emission surface may be inclined so as to extend radially inward as the distance from the incident surface increases along the center axis.

Furthermore, the above-described aspect may further include: a waveguide that receives, at an incident surface, the illumination light from the light source and that guides the illumination light to an emission surface through total internal reflection; and an outer diffusion element that is disposed so as to be opposed to the emission surface, wherein the waveguide may be formed into an annular shape extending over the entire circumference or partly in the circumferential direction about a center axis, and a transverse cross section of the waveguide may have a shape curved outward with respect to the center axis, from the incident surface toward the emission surface; and an emission surface of the outer diffusion element may be inclined so as to extend forward and radially inward.

By doing so, illumination light that is made to be uniform by the waveguide and that is emitted from the emission surface can be made to enter the outer diffusion element from the incident surface thereof, can be further scattered, and can be emitted. It is possible to cause the waveguide at the former stage, to highly efficiently guide uniform illumination light while suppressing scattering and to cause the outer diffusion element, at the latter stage, to scatter the guided illumination light, thus making it possible to highly efficiently perform uniform illumination in a wide region.

Furthermore, in the above-described aspect, the waveguide may be formed as a light diffusion element.

By doing so, more uniform illumination can be performed.

According to the present invention, an advantageous effect is afforded in that it is possible to improve illumination-light utilization efficiency while uniformly illuminating a wide region.

REFERENCE SIGNS LIST

20 light source device (light source)
30 illumination optical system
31, 37 diffusion element
32 incident surface
33 reflecting surface (deflection surface)
34 emission surface
35 waveguide member
38 deflection surface 39 outer diffusion element
40 incident surface
O optical axis (center axis)

The invention claimed is:

1. An illumination optical system comprising a diffusion element that diffuses illumination light entering from a light source, the diffusion element emitting the illumination light, wherein:

the diffusion element comprises a homogeneous medium in which fine particles of at least one kind are dispersed, the homogeneous medium being made of a material different from a material from which the fine particles are made, and the homogeneous medium comprising an optically transparent resin, the diffusion element includes:
an incident surface having an annular shape extending over an entire circumference or partly along a circumferential direction about a center axis, the incident surface being disposed at one end of the diffusion element in the direction of the center axis, and the illumination light from the light source being incident on the incident surface;
a deflection surface that is disposed so as to be opposed to the incident surface in the direction of the center axis, the deflection surface being inclined so as to extend toward a radially outer side, as a distance of the deflection surface from the incident surface increases along the center axis, at an angle greater than 0° and equal to or less than 45° with respect to the center axis, and so as to deflect the illumination light incident on the incident surface toward a radially outer side; and
an emission surface that is disposed closer to a radially outer side than the deflection surface is, the illumination light deflected at the deflection surface being emitted from the emission surface, and the emission surface being inclined so as to extend radially inward as a distance of the emission surface from the incident surface increases along the center axis, and the diffusion element satisfies the following conditional expressions:

$0.06 \leq \mu s(1/mm) \leq 20;$ $0.5 \leq g < 1;$ $0.005 \leq |n1-n2| \leq 0.5;$ $0.5 \leq d(\mu m) \leq 50;$ and $0.1 \leq c(\text{weight \%}) \leq 50,$ where $\mu s$ is a scattering coefficient of the diffusion element, g is an anisotropy parameter of the fine particles in the homogeneous medium, the anisotropy parameter being defined by an average of cosines of scattering angles when light is scattered by one of the fine particles, n1 is a refractive index of the resin, n2 is a refractive index of the fine particles of at least one kind, d is a particle size of the fine particles, and c is a mass concentration of the fine particles with respect to the resin.

2. The illumination optical system according to claim 1, wherein:
a width dimension of the deflection surface in a radial direction is larger than a width dimension of the light source; and
the incident surface is opposed to the light source and is disposed so as to be closer to the center axis than a center of the diffusion element is.

3. The illumination optical system according to claim 2, wherein:
the diffusion element has a protruding section that protrudes rearward along the direction of the center axis, at an outer side of a section of the incident surface opposed to the light source; and
the emission surface extends to the protruding section.

4. The illumination optical system according to claim 2, wherein the diffusion element has, at a front end of the deflection surface, a surface that is substantially parallel to the incident surface.

5. The illumination optical system according to claim 2, wherein the diffusion element has:
a flat section that extends forward, at a front end of the deflection surface; and
a surface that is substantially parallel to the incident surface, at a front end of the flat section.

6. The illumination optical system according to claim 1, wherein the deflection surface is disposed at such a position as to directly reflect the illumination light incident on the incident surface of the diffusion element.

7. The illumination optical system according to claim 6, further comprising a waveguide member, the waveguide member being a light diffusion element and comprising an optically transparent resin in which fine particles of at least one kind are disposed.

8. The illumination optical system according to claim 1, further comprising:
a waveguide that receives, at an incident surface, the illumination light from the light source and that guides the illumination light to an emission surface through total internal reflection; and
an outer diffusion element that is disposed so as to be opposed to the emission surface,
wherein:
the waveguide has an annular shape extending over an entire circumference or partly along a circumferential direction about a center axis, and a transverse cross section of the waveguide has a shape curved outward with respect to the center axis, from the incident surface toward the emission surface; and
an emission surface of the outer diffusion element is inclined so as to extend forward and radially inward.

9. The illumination optical system according to claim 8, wherein the waveguide comprises a light diffusion element.

10. The illumination optical system according to claim 1, wherein the deflection surface has a curvature.

11. The illumination optical system according to claim 1, wherein the deflection surface is inclined at an angle equal to or greater than 20° and equal to or less than 45° with respect to the center axis.

12. The illumination optical system according to claim 1, further comprising, between the light source and the incident surface, a waveguide member having an annular shape extending over an entire circumference or partly along a circumferential direction about the center axis, that guides, through total internal reflection, the illumination light emitted by the light source, and that causes the illumination light to be incident on the incident surface.

13. The illumination optical system according to claim 1, wherein:
the diffusion element comprises a waveguide having an annular shape extending over an entire circumference or partly along a circumferential direction about a center axis, and a transverse cross section of the diffusion element has a shape curved outward with respect to the center axis, from an incident surface toward an emission surface thereof; and the emission surface is inclined so as to extend radially inward as the distance from the incident surface increases along the center axis.

\* \* \* \* \*